United States Patent
Levene et al.

(10) Patent No.: US 10,677,730 B1
(45) Date of Patent: Jun. 9, 2020

(54) FAST MULTIPHOTON MICROSCOPE

(71) Applicant: APPLIKATE TECHNOLOGIES LLC, Weston, CT (US)

(72) Inventors: Michael Levene, Washington, DC (US); Richard Torres, East Haven, CT (US)

(73) Assignee: APLLIKATE TECHNOLOGIES LLC, Washington, DC (US)

( * ) Notice: Subject to any disclaimer, the term of this patent is extended or adjusted under 35 U.S.C. 154(b) by 0 days.

(21) Appl. No.: 16/523,698

(22) Filed: Jul. 26, 2019

Related U.S. Application Data

(60) Provisional application No. 62/800,161, filed on Feb. 1, 2019.

(51) Int. Cl.
*G01N 21/64* (2006.01)

(52) U.S. Cl.
CPC ..... *G01N 21/6458* (2013.01); *G01N 21/6486* (2013.01); *G01N 2021/6463* (2013.01); *G01N 2201/06113* (2013.01)

(58) Field of Classification Search
CPC .......... G01N 21/6458; G01N 21/6486; G01N 2021/6463; G01N 2201/06113
See application file for complete search history.

(56) References Cited

U.S. PATENT DOCUMENTS

| | | | |
|---|---|---|---|
| 6,687,000 B1 * | 2/2004 | White | G01N 21/6408 356/300 |
| 2009/0225383 A1 * | 9/2009 | Soeda | B41J 2/473 359/198.1 |
| 2010/0119262 A1 * | 5/2010 | Omori | F21V 29/677 399/220 |
| 2016/0150963 A1 * | 6/2016 | Roukes | A61B 5/6868 600/476 |
| 2018/0373009 A1 * | 12/2018 | Yuste | G02B 21/367 |

* cited by examiner

*Primary Examiner* — Marcus H Taningco
(74) *Attorney, Agent, or Firm* — Brown Rudnick LLP; Thomas C. Meyers

(57) ABSTRACT

The invention provides improved systems and methods for multiphoton microscopy including pixel clocking techniques for minimizing pixel integration time and providing consistent signal intensity with maximized imaging speeds. Various systems and method are described for optimizing laser repetition rate based on dye lifetime, combining polygonal mirror scanning and stage translation, using the laser pulse signal to time pixel collection, and minimizing laser pulses and dye usage based on signal to background ratios.

16 Claims, 2 Drawing Sheets

FAST MULTIPHOTON MICROSCOPE

RELATED APPLICATIONS

This application claims priority to U.S. Provisional Application No. 62/800,161, filed on Feb. 1, 2019, the content of which is hereby incorporated by reference in its entirety.

FIELD OF THE INVENTION

The invention relates to systems and methods for multiphoton microscopy.

BACKGROUND

Achieving high imaging speed is critical to enabling the incorporation of digital imaging in a clinical workflow. Digital slide scanning, or whole slide imaging (WSI), is increasingly used in clinical environments owing to the benefits it provides in terms of remote interpretation by experts, security and longevity for archiving, potentially higher review efficiency, and amenability to evolving tools for computer aided diagnosis. An important measure of functionality is the throughput of the digitalization instrument, most often quoted in terms of time required to scan a 15 mm×15 mm area and typically on the order of one to six minutes. Since slides are usually imaged serially on a given instrument, high throughput is desirable not only for ensuring pathologists have access to images as quickly as possible, but (perhaps most importantly) for reducing the cost-per-sample of the scanning instrument which may otherwise be prohibitively high.

Multiphoton microscopes (MPM) (e.g., as described in U.S. Pat. No. 5,034,613 to Denk et al.) have proven to be a valuable tool for biological research and offer a potential alternative for histologic analysis (and WSI) in clinical and research settings. In order to allow future clinical implementation of MPM in histologic analysis, existing speed limitations must be critically addressed.

Various aspects contribute to achievable image acquisition speeds in MPM. Systems typically comprise a laser source that produces ultrashort laser pulses of about 50 fs-2 ps, with a repetition rate of ~80 MHz. The light from the laser is focused by a microscope objective to a point inside the sample. This point is scanned across the sample by a system of mirrors placed upstream of the objective that may be mounted on galvanometers. The generated fluorescence is typically collected back through the objective lens and directed to one or more detectors by a series of dichroic and emission filters, or by collection optics positioned on the opposite side of the sample from the objective lens and directed to one or more detectors by a series of dichroic and emission filters. The generation of fluorescence in the sample occurs by the simultaneous absorption of two or more photons from the laser. The use of short pulses leads to high peak intensities for more efficient multiphoton absorption without requiring excessive average laser powers.

Galvanometers used for point scanning are typically comprised of mirrors mounted on shafts that rotate in either a linear or sinusoidal fashion, deflecting the beam in a line pattern. The typical multiphoton microscope scans one line of the sample in ~1 ms, with pixel dwell times on the order of ~1 us. The pixel clock, which determines when signal coming from the detectors gets assigned to a new pixel, is synced to the position of the scanning optics in order to create pixels of uniform size. Because the pixel dwell time is long compared to the time between laser pulses (typically 12 ns), many pulses will strike the sample during a given typical pixel dwell. It is therefore unimportant to count the number of pulses arriving per pixel. However, when imaging at much higher scan rates than the typical system, pixel dwell times may shorten to the point that the variation in the number of pulses per pixel leads to unwanted variation in the amount of fluorescence collected from pixel to pixel.

For microscopes that incorporate at least one resonant galvanometer for high-speed scanning, the non-linear, sinusoidal scan pattern of the resonant galvanometer results in a very large variation in the number of pulses per pixel. This creates pronounced inhomogeneity in image intensity across the field-of-view and limits the maximum rate that can be achieved for a given minimum number of pulses per pixel. The latter occurs because the sinusoidal movement of the mirror results in pixel collection that is slower at the edges of the field of view than at the midpoint of rotation where the speed is at its maximum. The inhomogeneity in image intensity translates to image quality limitations that limit the applicability of resonant galvanometer based MPM systems to diagnostic interpretation of tissue histology.

Spinning polygons have also been used to increase the rate of line scanning in point-scanning systems and do not suffer from the variable speed issues of standard or resonant galvanometers. Shack et al. (1979) described theoretical speed optimization using continuous wave lasers and spinning polygons for point scan imaging of biological samples by coupling it with continuous motion of perpendicularly oriented stage movement. The description refers to the potential for fast imaging, but beyond being theoretical, the description predates the invention of the multiphoton microscope and thus does not address aspects specific to the coupling of spinning polygons to multiphoton excitation.

Some multiphoton microscopes have used high-repetition-rate laser pulse trains in order to increase the speed of imaging or to lower the peak power in order to reduce photobleaching and photodamage. Amir et al. 2007 used a beamsplitter and a delay line to double the effective repetition rate of 23 MHz laser pulses, while Cheng et al. 2011 used multiple beamsplitters, resulting in a 4-fold increase in the 80 MHz pulse rate of the source laser. However, both Amir and Cheng focused the outputs of the beamsplitters onto different spots within the sample, such that the effective pulse rate for a single spot was unchanged from that of the source laser. Chu et al. 2003 used an ultrafast laser with a 2 GHz repetition rate for second harmonic imaging, but did not use this laser for multiphoton fluorescence imaging. Ni et al. 2008 used a series of beamsplitters and delay lines to image with a single scanning spot with an effective pulse repetition rate of 640 MHz-10.24 GHz, much faster than the lifetime of the fluorescent protein they were imaging. While that approach worked for the specific samples used, its general applicability with other samples and dyes is questionable due to excited-state absorption resulting in increased dark state population and photobleaching. Thus, no solution presented to date has been able to achieve a MPM with maximized speed that ensures maximal quality for detailed histologic evaluation in a timely fashion.

SUMMARY

The invention provides a multiphoton microscope with various features that enable efficient, high quality imaging at high speed of fluorescently labeled tissue samples. Systems and methods of the invention are of particular interest for diagnostic interpretation of tissue specimens. In some aspects, the design is specifically geared toward the fast multiphoton imaging of tissue specimens that have been processed with a method described in a prior patent application. The multiple components work in concert and all contribute to achieving high speed imaging using multiphoton microscopy with quality amenable to primary diagnostic interpretation. The combined features allow for image quality heretofore not achieved at the rates described herein. Accordingly, the systems and methods of the invention allow for practical histologic analysis from MPM with the quality and speed required for clinical use and large volume imaging for investigative purposes.

In certain aspects, systems and methods of the invention include a pixel clock configured such that each pixel integrates fluorescent photons generated by a fixed integer number of laser pulses, ranging from 1-20. In some aspects, methods of the invention include the use of a pulsed laser with a repetition rate that is similar to the lifetime of the dyes used in the object being imaged. Certain systems and methods of the invention include the use of a polygonal mirror for rapid scanning in one direction and a translational stage for moving the specimen in a direction perpendicular to that of the scan line generated by the rotating polygonal mirror. Some systems and methods of the invention include a pixel clock that is coordinated to the laser pulses such that the start of each pixel has a fixed time delay, which may be zero, with respect to the timing of the most recent laser pulse in order to minimize cross-talk between pixels due to the long exponential tail typical of fluorescence decays.

Systems and methods of the invention contemplate the minimization of pulses per pixel while maintaining the quality of images based on signal to background ratio and the use of sufficient fluorescent dye concentrations in a specimen to achieve a threshold of signal to background with a limited number of pulses but not more than needed so as to control cost of dyes and avoid fluorophore self-quenching and absorption of fluorescent photons.

Aspects of the invention include a variety of microscope configurations to increase efficiency, image quality, and speed in MPM and other imaging techniques. For example, a second laser may be employed incident upon the polygonal mirror along with a detector that collects the reflected signal which can then be used for tracking the mirror position for coordinating the pixel clock with scanning of the excitation spot in the sample. Group velocity dispersion in the microscope optics can be pre-compensated for to minimize the laser pulse width at the sample. Detector amplifiers that are balanced for speed and amplification and matched to the rate of pixel acquisition can be used in devices of the invention.

An appropriate wavelength can be selected for the simultaneous excitation (and detection) of both nuclear and protein fluorescent dyes to allow for combined imaging thereof. Laser power levels can be optimized to maximize optical resolution and minimize optical section thickness while maintaining desired signal to background levels. Systems and methods of the invention can include using a microscope objective that has a combination of high numerical aperture, large field-of-view, and very long working distance, and is optimized for imaging of specimens with normalized high refractive index such as by clearing techniques.

A detection filter combination can be used that can separate the emission of green-fluorescent protein dyes such as eosin from the emission of hematoxylin-like blue fluorescent nucleic acid dyes such as DAPI and Hoechst, so as to enable reproduction of the standard histologic stain of hematoxylin and eosin (H&E).

DETAILED DESCRIPTION

Figure 1A:
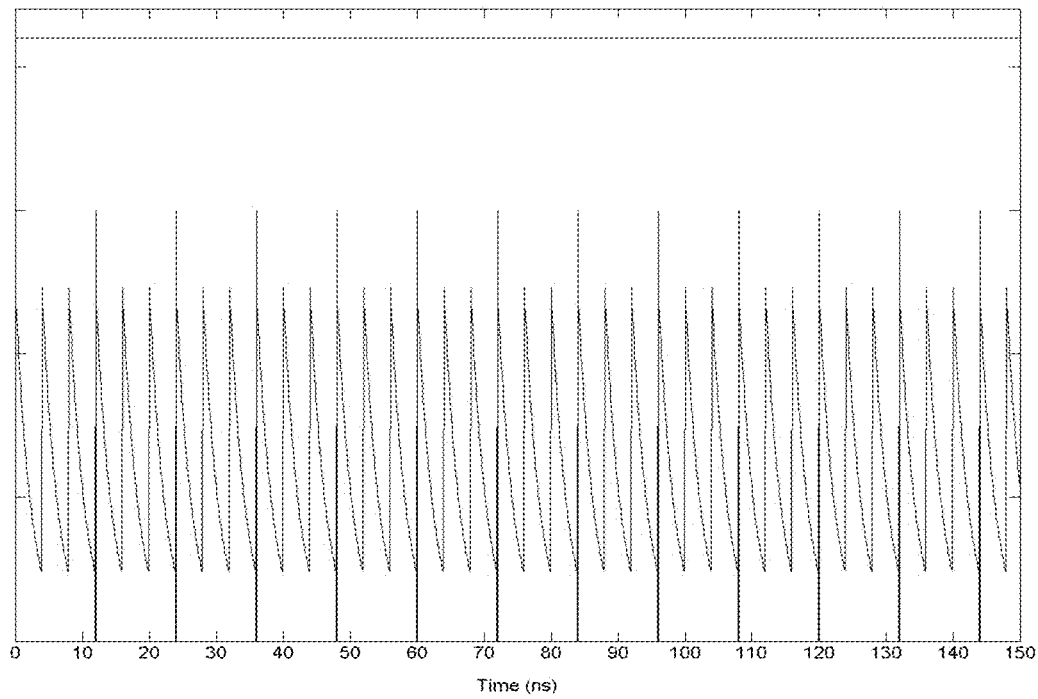
FIG. 1A shows a 12 ns pixel clock selected as an integral multiple of a laser 4 ns interpulse interval.

For a given image quality, determinants of maximum achievable speed include fluorescence lifetime of dyes, multiphoton pulse rate, beam movement efficiency including duty cycles and constancy of dwell-times, timing efficiency for coordinating laser beam movement and data acquisition, non-imaging time (e.g. sample positioning time), light collection efficiency (including objective lens numerical aperture and signal collection pathway), and related signal-to-noise aspects such as dye efficiency, dye concentration, detector efficiency, and detector and other noise sources. The various features employed in the invention have been devised to address these determinants in order to guarantee high image quality at high speed.

Pixel Dwell Times that are Integer Multiples of the Laser Interpulse Interval

Maximizing imaging speed requires minimizing the integration time per pixel known as the pixel dwell time. Decreasing the pixel dwell time results in fewer laser pulses striking the sample pixel. If the pixel dwell time is not an integer number times the interpulse interval of the excitation laser, the number of laser pulses striking the sample will vary from pixel to pixel. Shorter pixel dwell times result in fewer laser pulses striking the sample per pixel on average, leading to larger variation in signal intensity from pixel to pixel, even for a uniform sample. One aspect of the invention is the use of a pixel clock that results in uniform pixel dwell times that are a fixed integer number times the interpulse interval of the excitation laser.

The number of pulses at which the effect of non-fixed integer number of pulses results in variability with visually detectable image degradation is dependent on the specific application. For visual analysis of biologically derived images such as for histologic interpretation, pixel-to-pixel variability of 5% or more stemming from interpulse integer variability may produce detectable image degradation. As such, when pixel dwell times are in the range of 20 interpulse intervals, pulse counting becomes increasingly relevant for image quality. In a preferred embodiment, the pixel dwell time is 1-12 integer times the length of the interpulse interval. In various embodiments, the pixel dwell time can be about 2 to about 10 times, about 2 to about 100 times, about 2 to about 6 times, about 2 times, about 4 times, about 6 times, or about 8 times the length of the interpulse interval. Where an integer number is referred to herein with regard to the relationship between pixel dwell time and interpulse interval, one of ordinary skill in the art would understand that practically achievable precision must be taken into account. Accordingly, pixel dwell times of 2 to 100 times the interpulse interval, for example, should be understood to include each integer between 2 and 100 to a degree of decimal places required to achieve the desired effect of equally distributing pulses among the imaged pixels. As such the precision of the dwell time to interpulse interval relationship should be defined such that any deviations (e.g., imprecision at several decimal places) from a strict integer relationship do not result in significant pulse variation among the imaged pixels.

FIG. 1A shows the result of a uniform pixel dwell time that is an integer multiple of the laser interpulse interval. The blue line shows the fluorescence signal level with time from a uniform sample as a result of excitation by laser pulses with an interpulse interval of 4 ns. The black vertical lines represent the start of each pixel dwell time of 12 ns, 3 times the interpulse interval. Each pixel dwell integrates over a time period with a fixed relation to the laser pulse train, resulting in uniform pixel intensity as shown by the black horizontal line at the top of the figure. Even if the pixel clock is shifted slightly in time relative to the laser pulse train, the signal will still be uniform.

Figure 1B:
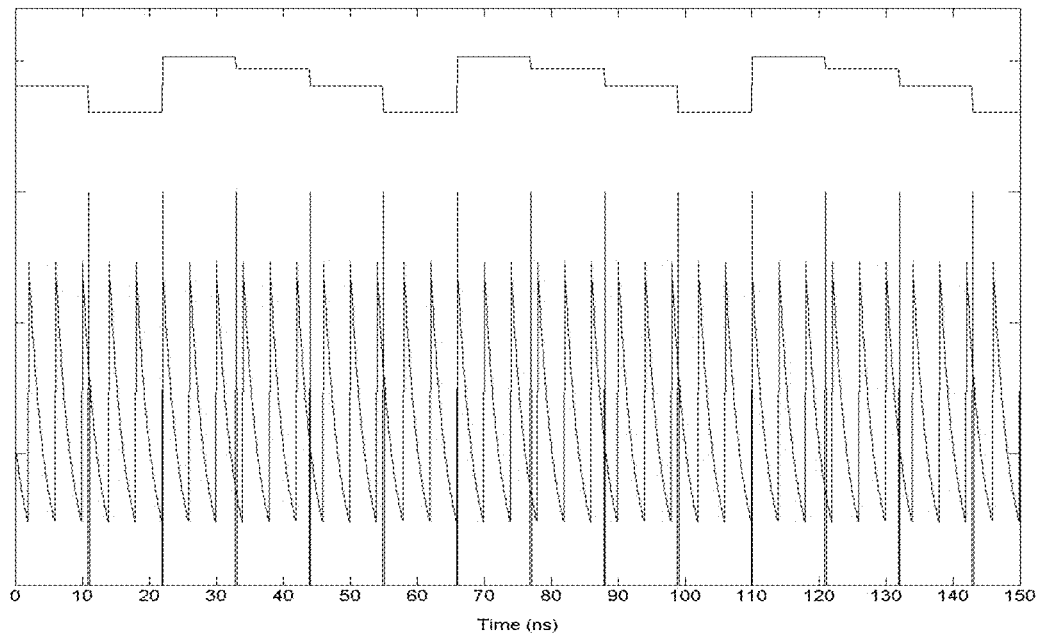
FIG. 1B shows an 11 ns pixel clock that is a non-integer multiple of the laser interpulse interval.

FIGS. 1A and 1B show the effect of non-integer pixel dwell times. In FIG. 1A, a 12 ns pixel clock (vertical lines touching the X-axis) is an integral multiple of the laser 4 ns interpulse interval. The integration of the fluorescence signal (wave lines on graph) results in uniform pixel intensities (line along top of the graph) for a uniform sample. In FIG. 1B, a 11 ns pixel clock is a non-integer multiple of the laser interpulse interval, resulting in non-uniform pixel intensities FIG. 1B shows the results of a uniform pixel dwell time that is not an integer multiple of the laser interpulse interval. The signal wave line on the graph shows the fluorescence signal level with time from a uniform sample as a result of excitation by laser pulses with an interpulse interval of 4 ns. The vertical lines touching the x-axis of the graph represent the start of each pixel dwell time of 11 ns, or 2.75 times the interpulse interval. The resulting pixels shift their integration window with respect to the laser pulse train, resulting in non-uniform pixel intensity as shown in the black line across the top of the figure.

Optimizing Laser Repetition Rate Based on Lifetime of Fluorescent Dyes being Imaged Choosing laser repetition rates that result in inter-pulse intervals that are much shorter than the fluorescence lifetime can lead to unwanted effects, such as excited state absorption and increased photobleaching and/or photodamage, and result in inefficient dye excitation with consequent reductions in quality. Choosing laser repetition rates with inter-pulse intervals that are much longer than the fluorescence lifetime results in slower imaging speeds. With the number of pulses per pixel fixed according to the minimum required total collected signal per pixel, higher repetition rates lead to faster imaging. If the number of pulses per pixel is not fixed, the variation in the number of laser pulses from pixel to pixel may be minimized by increasing the number of pulses per pixel through the use of a higher repetition rate laser. The repetition rate of the laser can be chosen such that the interpulse interval, the time between laser pulses, is similar to the lifetime of the fluorescence dyes. In order to avoid one laser pulse exciting dye molecules that are already in the excited state due to the previous laser pulse, the inter-pulse interval should be on the order of the dye lifetime. In a preferred embodiment, the interpulse interval should be somewhat longer than the dye lifetime because the exponential decay of the fluorescence lifetime has a long tail to its distribution. For example, the inter-pulse interval can be 1-3 times the lifetime of the longest lifetime dye present in the sample. The nuclear fluorescent dye DAPI has a fluorescence lifetime of 1.6 ns, while the fluorescent protein dye Eosin has a lifetime of 2.4 ns. Applying the above embodiments in such a case would result in selecting a laser with a repetition rate of 250 MHz which allows sufficient time for the vast majority of eosin molecules to return to ground state, but minimizes the collection time during which there is no effective signal acquisition.

Combination of Polygonal Mirror and Translating Stage for Rapid Point Scanning of Multiphoton Laser In microscopy techniques discussed herein, the laser is scanned across a sample in order to form an image. That scanning can be done by mirror(s) mounted to one or more galvanometers, by one or more mirrors mounted in a piezo-driven mirror mount, by translation of the stage in one or more directions, or by any other method or combination of methods capable of moving the focused laser spot across the sample. In a preferred embodiment, the pulsed laser beam is rapidly scanned in angle by a spinning polygon with mirrored facets, such as those currently available from Lincoln Laser Company, Phoenix, Ariz.

The scanned beam can be imaged to the entrance pupil of a microscope objective using a scan lens and a tube lens. In some embodiments, the scan lens is a telecentric F-theta lens. Alternatively the scan lens may be an F-theta lens, or any suitable lens system that, when used together with the tube lens, effectively images the angle-scanned beam from the surface of the spinning polygon mirror to the entrance pupil of the microscope objective. The microscope objective focuses the beam to a spot in the sample contained within the sample cartridge. The angle scanning of the beam by the spinning polygon results in the spot scanning in a line across the sample.

A stage may be designed to hold a sample in place and to perform a translation of the sample in a direction largely perpendicular to the direction the laser spot is scanning due to the motion of the spinning polygon mirror. Thus, as the laser spot is scanned across the sample by the polygon mirror, the stage moves the sample in the orthogonal direction to the scan line, resulting in the imaging of a strip of sample, the width of which is determined by the extent of the laser scan and the length of which is determined by the length of the stage scan. The stage may also be capable of fine scanning in the direction of focus of the microscope objective in order to change the focal plane. Alternatively, or in addition, the objective lens may be mounted on a focusing apparatus. The fine scanning in the direction of focus can occur between sessions of image acquisition or during an image acquisition session, the latter resulting in collection of image data that is in a line that is not perpendicular to the either the sample holding stage or the objective. The stage can also be capable of scanning in largely the same direction as the moving laser focus in order to image multiple strips of the object being imaged (e.g., a tissue sample), the resulting images of which may be assembled into a mosaic using software during or after image acquisition. A scan pattern with partial overlap between successive strips may be chosen in certain embodiments to aid in the later assembly of the mosaic from the scan images. The stage translation and the polygon rotational speeds may be coordinated such that the distance travelled by the stage during the period the laser is reflected off a given polygon facet is equal to the desired length of one dimension of a pixel.

In some embodiments the desired pixel dimension in the translated stage direction can be the same as the pixel dimension in the polygon rotation direction. In other embodiments the pixel dimension in the translated stage dimension can be longer or shorter than in the rotating mirror scanned dimension. That may be done so as to reduce noise by averaging adjacent pixels along the polygon scanning direction. This may reduce noise differently than averaging of signal across multiple axes simultaneously, which would allow independent optimization of imaging speed in different axes. In some embodiments the pixel dimension in the translated stage dimension can be an integer multiple of the dimension in the rotating mirror scanned direction.

Using a Laser Pulse Signal to Time Pixel Collection

Each laser pulse excites a fluorescence signal that decays exponentially in time. In some cases, the long tail of this decay may result in some fluorescent photons generated by the last pulse in a given pixel dwell arriving at the detector during the subsequent pixel dwell. That cross-talk between pixels may act to blur the signal from one pixel into the adjacent pixel. A computer can be used to assign the signal from the detectors to pixels in sequence. Timing the start of each pixel dwell time to coincide with the peak fluorescence signal from the first laser pulse in that pixel dwell time minimizes the cross-talk between pixels. As such, in one embodiment of the invention a synchronization signal from the laser can be used to trigger a detector signal digitization board to assign collected fluorescence for a set period of time to a particular pixel. Different embodiments may use different polygon scanning speeds and different numbers of laser pulses per pixel. For the same scanning speed, using larger numbers of pulses per pixel, such as 5 or 10, would result in larger pixels.

In certain embodiments, the relationship between the start of pixel collection and the laser peak pulse can be manipulated to help minimize pixel-to-pixel cross talk. As such, in some embodiments the data acquisition board can be triggered to record signal from the detectors by a separate clock with a rate that is an integer multiple of the pixel rate. Such an arrangement requires sufficient precision and accuracy in both the laser pulse timing and the separate clock to ensure some pixels do not suffer from artifacts of pulse number variation.

Minimization of Number of Pulses Based on Signal to Background

In certain aspects systems and methods of the invention relate to the determination and use of a minimal number of pulses that preserve a desired degree of contrast and clarity for the fluorescent images derived. That determination can be based on the subjective visualization of acquired images such that images collected with many pulses per pixel may be compared to images with progressively smaller number of pulses per pixel and judged as to overall ability to discern features of potential interpretive importance for say pathologic diagnosis. In certain embodiments, that subjective visualization can be translated to a measured signal to background (SBR) as follows: For the background, areas devoid of staining tissue are collected using MPM and the standard deviation of the signal, or other similar measure of variation such as variance, in the otherwise dark regions may be used as a measure of background noise. That measure of background noise is compared to the average maximum intensity of multiple areas that contain known bright features. For a nucleic acid stain, this may be lymphocyte nuclei or other portions of nuclei. For a protein stain, this may be red blood cells.

Images with SBR lower than about 20 appear undesirable for analysis whereas those with SBR greater than about 50 do not typically show additional improvement from standard histologic stains. Thus, target SBR for optimization using systems and methods described herein can be between 20 and 50. In some cases a SBR of 50 may be desirable. In other cases a SBR of 40 may be desirable. In other cases a SBR of 30 may be desirable. In other cases a SBR of 20 may be sufficient.

Once the threshold is established, then it is possible to analyze the same tissue sample in the same manner while varying the number of pulses per pixel. With the preparation method and instrument implementation configuration described herein, it has been determined that between 2 and 8 pulses are the required minimum for achieving the desired SBR.

Use of Minimal Amount of Dyes that Yield Threshold of Signal to Background with Few Pulses A principal concern in diagnostic imaging is cost. Some dyes are expensive and can form a large part of the overall processing cost which could affect the usability in high volume environments such as for clinical imaging use. Determination of the optimal dye concentration to use for high speed, high quality imaging can be based on the measurement of SBR at a given pulses per pixel as a function of dye concentration. By optimizing dye concentration, waste can be avoided and costs reduced using the methods described herein.

Figure 2:
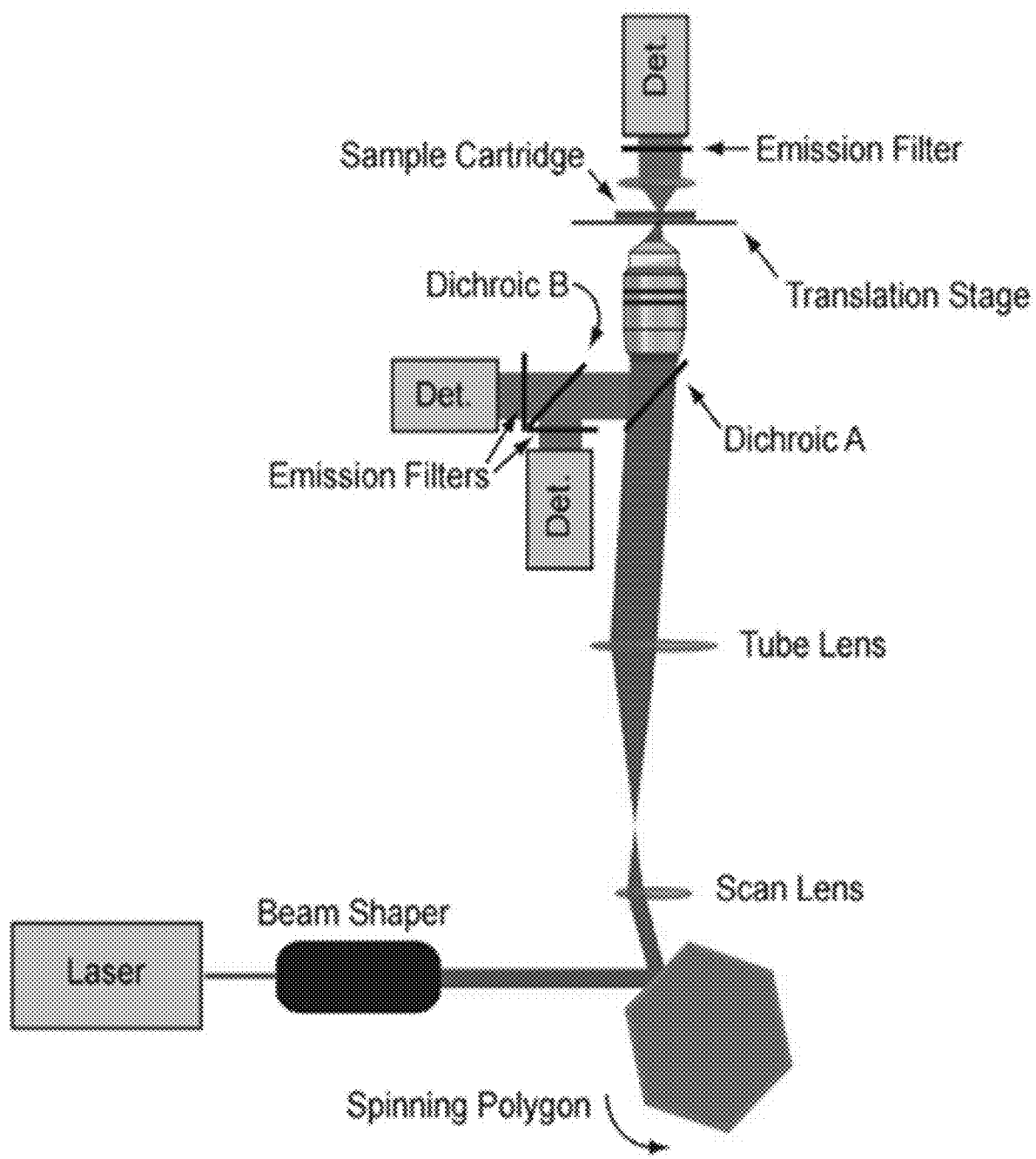
FIG. 2 shows a schematic of a microscope according to certain embodiments.

FIG. 2 shows a schematic of a preferred embodiment of a microscope of the invention. The microscope consists of a laser source suitable for multiphoton excitation of the dyes used for labeling the sample. The laser may be a Ti:Sapphire laser, or a fiber laser, or any other laser capable of producing ultrashort laser pulses. In various embodiments, pulses ranging from several picoseconds to less than 150 fs may be used. In some embodiments, the light from the laser passes through a beam shaping system that consists of a series of lenses and expands the beam to the required beam width to effectively illuminate the back aperture of the microscope objective that focuses the laser to a spot on the sample. The laser may have a fixed center wavelength, as is common with fiber lasers, or it may be broadly tunable, as is common with some Ti:Sapphire lasers. In a preferred embodiment, the laser would generate laser pulses with pulse widths<150 fs with center wavelength chosen for optimum excitation of dyes. In a preferred embodiment, the center wavelength is selected to optimally simultaneously excite both 4',6-diamidino-2-phenylindole (DAPI) and eosin, which has been determined to be between 740 and 820 nm, and more preferably the wavelength can be selected to reduce excitation of unbound dye, determined to be between 760 and 800. In certain embodiments the wavelength may be selected to be between 760 and 780. In some embodiments the wavelength may be 765 nm. In other embodiments the wavelength may be 780 nm, 770 nm, or 800 nm.

As shown in FIG. 2, the sample can be illuminated from below in what is commonly referred to as an "inverted microscope." Alternatively, the sample may be illuminated from above in what is commonly known as an "upright microscope."

Fluorescent light can be collected by the objective lens, reflected from a dichroic mirror and sent to one or more detectors. In some cases, additional lenses or mirrors may be used to efficiently collect the fluorescent light to the detectors. A second dichroic mirror may be used to send different color fluorescence to a different channel. For example, in a preferred embodiment for imaging Eosin and DAPI, Dichroic A is a 735 long pass, Dichroic B is a 550 short pass, Emission filter 1 is a 550 short pass, and Emission filter 2 is a bandpass for wavelengths 550 nm-665 nm. Other filters may be chosen as appropriate by one skilled in the art.

In some embodiments, an additional detector and associated collection optics may be used on the opposite side of the sample chamber from the objective lens to detect transmitted light signal to increase the detection efficiency of the fluorescence signals or of second harmonic generation signals by the use of additional detectors. A lens or series of lenses may be used to focus the transmitted light onto the detector (s), and appropriate dichroic and emission filters may be used. The detectors may be any detector sensitive to appropriate wavelengths of the fluorescence or second harmonic signals, such as photomultiplier tubes. In some embodiments the additional detector on the opposite side of the sample from the objective lens is used to collect second harmonic generation, the non-fluorescent signal generated by non-centrosymmetric molecules in response to short pulsed laser excitation and useful for characterizing collagen in tissue specimens.

A computer can be used to send and receive control signals to and from the scanning system. In a preferred embodiment, the computer sends a signal to the polygon that controls the speed of rotation. In a preferred embodiment, the computer also receives a signal from the polygon each time a new facet passes the laser to determine when a new line in the image has begun. In a preferred embodiment this signal is generated by means of a low power laser incident on the polygon mirror and reflected onto a diode or other light detector, which in turn sends an electrical signal to the computer and from which the polygon position can be determined. In a preferred embodiment the incident laser is directed towards the facet that is adjacent to the facet upon which the pulsed laser is directed. This will ensure the most accurate timing by addressing small potential differences in the facet dimensions. A fixed period of time, which may be zero but is proportional to the rate of polygon rotation and may include electric system delays, is set to transpire before data collection begins.

As one skilled in the art would recognize as necessary or best-suited for the systems and methods of the invention, systems and methods of the invention include one or more computers that may include one or more of processor (e.g., a central processing unit (CPU), a graphics processing unit (GPU), etc.), computer-readable storage device (e.g., main memory, static memory, etc.), or combinations thereof which communicate with each other via a bus.

A processor may include any suitable processor known in the art, such as the processor sold under the trademark Core by Intel (Santa Clara, Calif.) or the processor sold under the trademark Ryzen by AMD (Sunnyvale, Calif.).

Memory preferably includes at least one tangible, non-transitory medium capable of storing: one or more sets of instructions executable to cause the system to perform functions described herein (e.g., software embodying any methodology or function found herein); data (e.g., portions of the tangible medium newly re-arranged to represent real world physical objects of interest accessible as, for example, content including images or text for news articles); or both. While the computer-readable storage device can in an exemplary embodiment be a single medium, the term "computer-readable storage device" should be taken to include a single medium or multiple media (e.g., a centralized or distributed database, and/or associated caches and servers) that store the instructions or data. The term "computer-readable storage device" shall accordingly be taken to include, without limit, solid-state memories (e.g., subscriber identity module (SIM) card, secure digital card (SD card), micro SD card, or solid-state drive (SSD)), optical and magnetic media, hard drives, disk drives, and any other tangible storage media. Any suitable services can be used for storage such as, for example, Amazon Web Services, memory of a server, cloud storage, another server, or other computer-readable storage. Cloud storage may refer to a data storage scheme wherein data is stored in logical pools and the physical storage may span across multiple servers and multiple locations. Storage may be owned and managed by a hosting company. Preferably, storage is used to store records as needed to perform and support operations described herein.

Input/output devices according to the invention may include one or more of a video display unit (e.g., a liquid crystal display (LCD) or a cathode ray tube (CRT) monitor), an alphanumeric input device (e.g., a keyboard), a cursor control device (e.g., a mouse or trackpad), a disk drive unit, a signal generation device (e.g., a speaker), a touchscreen, a button, an accelerometer, a microphone, a cellular radio frequency antenna, a network interface device, which can be, for example, a network interface card (NIC), Wi-Fi card, or cellular modem, or any combination thereof.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A multiphoton microscope comprising:
a pulsed light source;
a focusing system operable to focus light pulses from the pulsed light source onto a sample on a sample stage;
a scanning system operable to move a focal point of the light pulses relative to the sample; and
a pixel clock operable to assign fluorescence signal to each pixel in a recorded image wherein each pixel integrates signal over a fixed integral number of light pulse interpulse intervals.

2. The multiphoton microscope of claim 1 wherein the scanning system comprises a spinning polygon mirror.

3. The multiphoton microscope of claim 2 wherein the scanning system is operable to perform a translation of the sample stage in a direction perpendicular to a scanning direction of the spinning polygon mirror to image a strip of sample having a width defined by the spinning polygon mirror scan and a length defined by the sample stage translation.

4. The multiphoton microscope of claim 1 wherein the integral number of light pulses is between 1 and 100.

5. The multiphoton microscope of claim 1 wherein the pulsed light source comprises a pulse repetition rate of about 70 MHz to about 1 GHz.

6. The multiphoton microscope of claim 5 wherein the pulsed light source is a laser.

7. The multiphoton microscope of claim 5 wherein the pulsed light source comprises an ultrafast laser, a beamsplitter, and a delay line.

8. The multiphoton microscope of claim 1 wherein the light source interpulse interval is between about 1 and about 3 times a fluorescent lifetime of a fluorescent dye in the sample.

9. A method for imaging a sample using a multiphoton microscope, the method comprising:
 loading a sample that has been exposed to a fluorescent dye into the multiphoton microscope, the multiphoton microscope comprising:
  a pulsed light source;
  a focusing system operable to focus light pulses from the pulsed light source onto a sample on a sample stage;
  a scanning system operable to move a focal point of the light pulses relative to the sample; and
  a pixel clock operable to assign fluorescence signal to each pixel in a recorded image over a pixel dwell time;
 imaging the sample using the multiphoton microscope wherein the pixel dwell time is a fixed integral number of light pulse interpulse intervals.

10. The method of claim 9 wherein the scanning system comprises a spinning polygon mirror.

11. The method of claim 10 wherein imaging the sample comprises the scanning system performing a translation of the sample stage in a direction largely perpendicular to a scanning direction of the spinning polygon mirror to image a strip of sample having a width defined by the spinning polygon mirror scan and a length defined by the sample stage translation.

12. The method of claim 9 wherein the integral number of light pulses is between 1 and 100.

13. The method of claim 9 wherein the pulsed light source is pulsed at a rate of about 70 MHz to about 1 GHz.

14. The method of claim 13 wherein the pulsed light source is a laser.

15. The method of claim 13 wherein the pulsed light source comprises an ultrafast laser, a beamsplitter, and a delay line.

16. The method of claim 9 wherein the light source interpulse interval is between about 1 and about 3 times a fluorescent lifetime of the fluorescent dye.

* * * * *

UNITED STATES PATENT AND TRADEMARK OFFICE
CERTIFICATE OF CORRECTION

| | |
|---|---|
| PATENT NO. | : 10,677,730 B1 |
| APPLICATION NO. | : 16/523698 |
| DATED | : June 9, 2020 |
| INVENTOR(S) | : Michael Levene et al. |

It is certified that error appears in the above-identified patent and that said Letters Patent is hereby corrected as shown below:

On the Title Page

(73) Assignee should read:
APPLIKATE TECHNOLOGIES LLC, Washington, DC (US)

Signed and Sealed this
Twenty-third Day of August, 2022

Katherine Kelly Vidal
*Director of the United States Patent and Trademark Office*